United States Patent [19]

Seldin

[11] 4,189,835

[45] Feb. 26, 1980

[54] METHOD OF DENTAL SURVEYING

[75] Inventor: Edward B. Seldin, Boston, Mass.

[73] Assignee: Massachusetts General Hospital, Boston, Mass.

[21] Appl. No.: 846,202

[22] Filed: Oct. 27, 1977

[51] Int. Cl.² .............................................. A61C 11/00
[52] U.S. Cl. ...................................... 433/214; 433/55
[58] Field of Search .............................. 32/20, 21, 32; 33/174 D

[56] References Cited

U.S. PATENT DOCUMENTS

| 1,753,965 | 4/1930 | Ralph | 32/32 |
| 2,618,068 | 11/1952 | Apple | 33/174 D |

*Primary Examiner*—Louis G. Mancene
*Assistant Examiner*—John J. Wilson
*Attorney, Agent, or Firm*—Richard J. Birch

[57] ABSTRACT

A dental surveyor and method therefor for use in preoperative evaluation of the rotational and translational movements required for corrective surgery are disclosed. The dental surveyor has a movable stylus or scribe that can be selectively positioned with respect to articulated mandibular and/or maxillary dental models. When the models are articulated in the two positions representing the malocclusion and the proposed corrective occlusion, the movable stylus provides a means for marking and thereby visually identifying the relative locations of a point of anatomical interest in the two positions.

4 Claims, 10 Drawing Figures

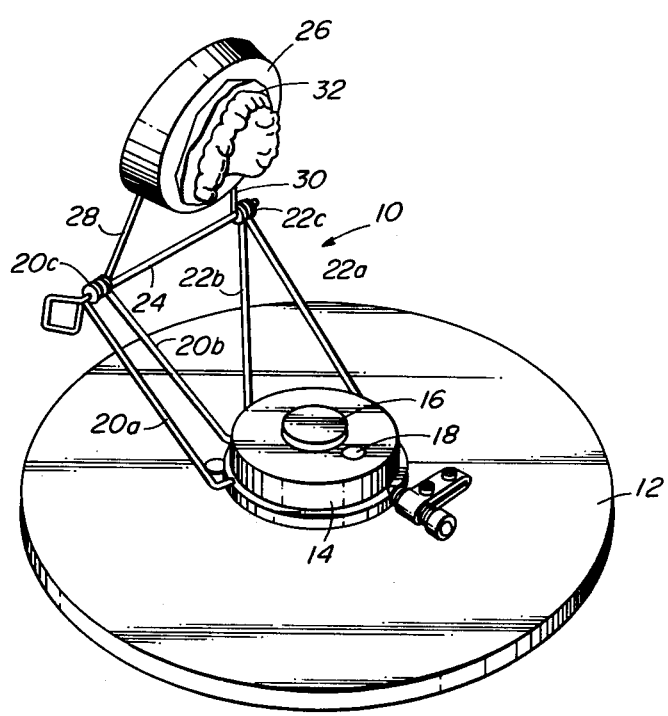
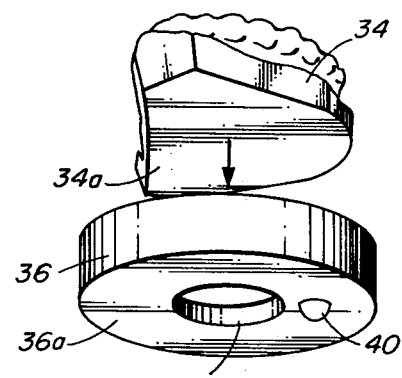
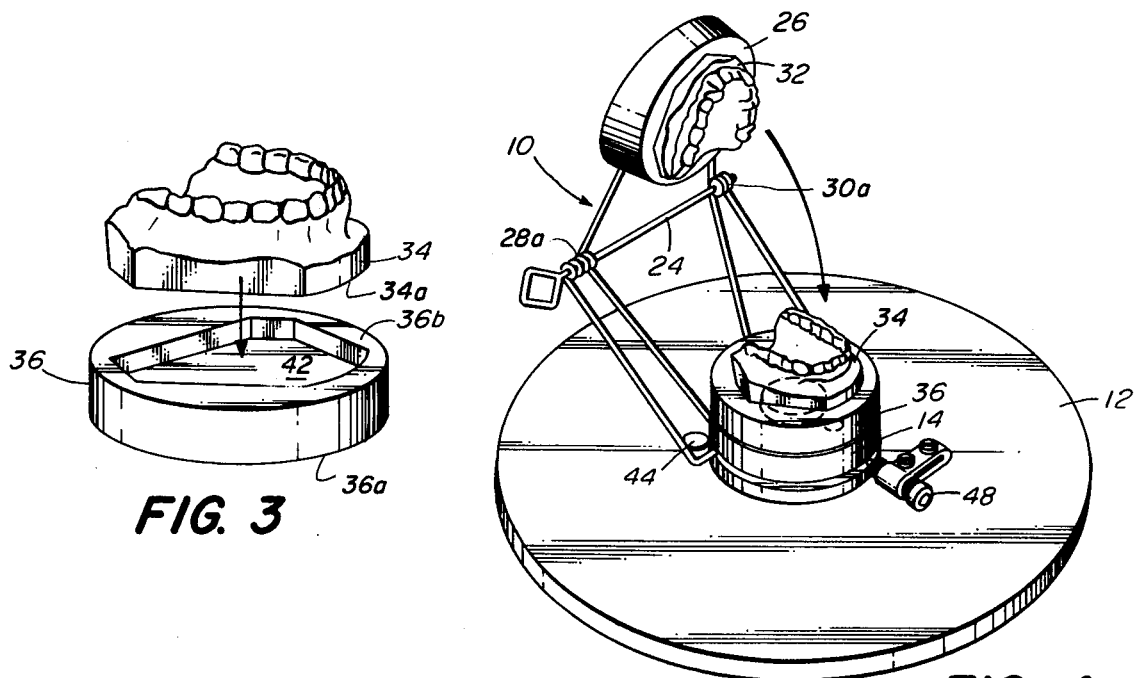
FIG. 1
FIG. 2
FIG. 3
FIG. 4

METHOD OF DENTAL SURVEYING

CROSS-REFERENCE TO RELATED APPLICATION

The present application is related to my co-pending application for a Method and Apparatus for Evaluating Anomalies of Facial Bilateral Symmetry filed Oct. 27, 1977 as Ser. No. 845,934.

BACKGROUND OF THE INVENTION

This invention relates to preoperative evaluation techniques and more particularly to a dental surveyor and method of using the surveyor for analyzing the rotational and translational movements that are required for correcting the patient's occlusion.

The category of non-critical osteotomies include all of the surgical procedures involving whole arch movements in which proximal and distal segments slide on one another such that bony contact is maintained and satisfactory healing is anticipated without special measures. This category involves (1) Le Fort I osteotomies, (2) oblique osteotomies, and (3) Obwegeser sagittal splits.

Various types of work-up techniques are available to the surgeon for different kinds of deformities. Certain techniques are better than others in terms of the corrective movements that they best measure. Dental models, although confined to dentoalveolar structures, nonetheless accurately document the anatomy they record in all three dimensions. When the mandibular and maxillary models are mounted on an articulator in the two positions representing the malocclusion and the proposed corrective occlusion, they display in three dimensional from the desired information for the corrective surgery. However, in order to fully analyze the proposed corrective surgery during a work-up, it is desirable to convert the three dimensional information into the rotational and translational movements that are needed to achieve the necessary jaw movements through surgery.

It is accordingly a general object of the invention to provided an apparatus and method for obtaining rotational and translational movements from articulated three dimensional dental models;

It is a specific object of the invention to provide a dental surveyor and method therefor that utilizes the three dimensional information contained in articulated dental models.

It is another object of the invention to provide an apparatus that produces a visual indication on the dental models of the movements, both rotational and translational, of selected points of anatomical interest.

It is a feature of the invention that the apparatus thereof can be employed in conjunction with a wide variety of dental models.

It is another feature of the invention that the apparatus thereof allows the surgeon to identify and visually mark all anatomical points of interest that lie within preselected horizontal and vertical planes which intersect the articulated dental models.

It is still another feature of the invention that the apparatus thereof can be fabricated from relatively simple and inexpensive hardware.

BRIEF DESCRIPTION OF THE INVENTION

Dental models are made of the patient's upper and lower jaws. The maxilla model is mounted on the upper portion of a single hinge axis articulator. Two locking templates that can be removably mounted on the base of the articulator and positionally referenced thereto are prepared using the mandibular model as a male casting element. The mandibular model is mounted on the articulator first in a position corresponding to the malocculsion and a cast is then made of the base of the model. The resulting female cast of the model base includes means for positionally referencing the cast to the base of the articulator. The cast can then be used as a template to accurately locate and lock the mandibular model at the position representing the malocclusion.

The same casting technique is employed to produce a template that locates and locks the mandibular model at the position representing the proposed corrective occlusion. By using the two locking templates on the articulator, the surgeon can accurately and repeatedly locate the mandibular model at both the malocclusion and corrected occlusion positions without reference to any scalar measurements.

The mandibular and maxillary models are mounted on the articulator using one of the locking templates. The dental surveyor is then secured to the maxillary model. The dental surveyor has a movable stylus or scribe assembly that can be rotated around a vertical axis through the two dental models and then locked at a selected rotational position. The stylus assembly is then adjusted vertically to position a movable stylus at a selected vertical elevation with respect to either the mandibular or maxillary model. Thereafter, the stylus is moved into marking engagement with the model. Once the model is marked, the stylus is withdrawn from contact with the model. However, the stylus itself is not moved with respect to the previously preselected vertical and rotational positions of the stylus assembly.

The mandibular model and template are now removed from the articulator and the mandibular model is remounted on the articulator using the other template. When the stylus is moved back into marking engagement with the model it takes a new mark that shows the movement, if any, of the previously marked point(s) of anatomical interest. The direction and amount of movement can be determined by drawing a line between the two marked points and measuring the translational displacements of the point of anatomical interest. This process can then be repeated in order to determine the rotational and translational movements of other points of anatomical interest.

Having briefly discussed the method and general apparatus of my invention, I will now describe in detail a preferred embodiment of my invention, selected for purposes of illustration and shown in the accompanying drawings, in which:

FIG. 1 is a view in perspective showing an articulator mounted on a base plate;

FIG. 2 is a view in perspective from below of a mandibular model and a locking template;

FIG. 3 is a view in perspective from above showing the locking fit of the FIG. 2 mandibular model within the locking template;

FIG. 4 is a view in perspective similar to that shown in FIG. 1, but with the addition of the mandibular model mounted on the articulator;

A DETAILED DESCRIPTION OF A PREFERRED EMBODIMENT

Figures 5, 6:
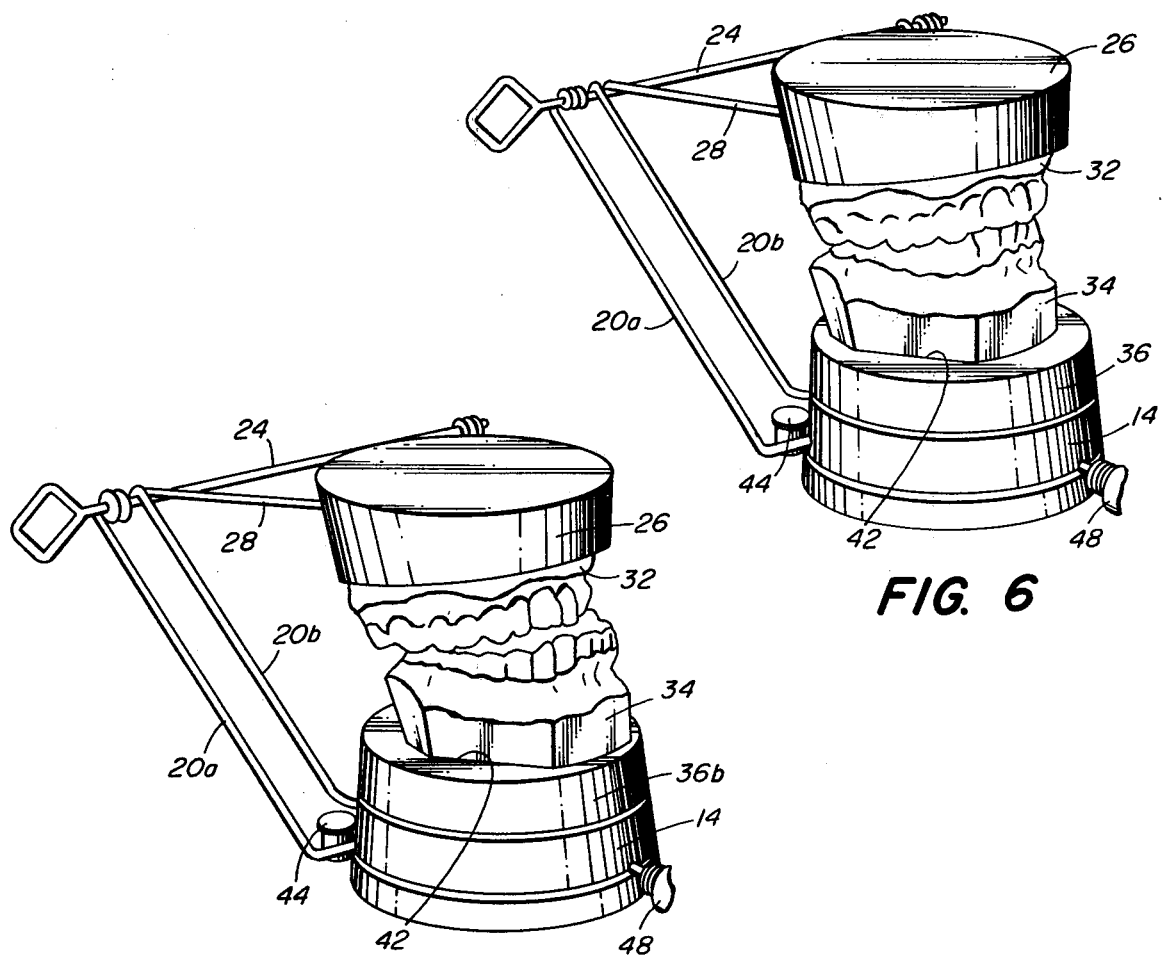
FIG. 5 is a view in perspective shows the mandibular model mounted on the articulator in the malocclusion position.
FIG. 6 is a view in perspective showing the mandibular model mounted on the articulator in the proposed corrective occlusion position.

Turning now to the drawings and in particular to FIGS. 1-4 thereof, there is shown a dental articulator indicated generally by the reference numeral 10, that is removably mounted on a mounting plate 12. The articulator 10 comprises: an articulator base 14 having a locating pin 16 and a locating dimple 18; a pair of wire pivot frame arms 20a-20b and 22a-20b which define circular bearings 20c and 22c, respectively; a pivot rod 24 that is removably positioned within bearings 20c and 22c; and a dental cast holder 26 that is rotatably mounted with respect to pivot rod 24 by means of cantilever pivot arms 28 and 30 which terminates in corresponding bearings 28a and 30a through which extends the previously mentioned pivot rod 24.

The articulator upper cast holder 26 is designed to accommodate and hold a dental model 32 of the patient's upper jaw. The articulator base 14 also is designed to accommodate and hold a model 34 of the lower jaw, but with the addition of an intermediate locking template 36 as shown in FIGS. 2-4. The locking template 36 has a central aperture 38 that corresponds in both size and shape to the upwardly extending locating pin 16 on the articulator base 14. In addition, the bottom surface 36a of the locking template is provided with a downwardly extending, hemispherical locking pin 40 that corresponds in both size and shape to the dimple 18 formed in articulator base 14. Thus, when the locking template 36 is assembled in superimposed relation on the articulator base 14, as shown in FIG. 4, the locking template 36 is accurately located and positionally referenced to the articulator base 14.

Looking at FIG. 3, the upper surface 36b of the locking template has formed therein a receptacle or template 42 having the same size and configuration as the base 34a of the mandibular model 36. Therefore, when the base 34a of the mandibular model is positioned within receptacle 42, as indicated in FIG. 3 by the arrow, the mandibular model is accurately located within and positionally referenced with respect to the locking template 34 which in turn is positionally referenced to the articulator base 14.

Given this physical arrangement, it will be appreciated that the upper and lower dental models 32 and 34, respectively, are accurately positioned with respect to each other by means of the articulator which permits movement of the upper model 32 vertically around the horizontal pivot axis provided by pivot rod 24. This movement is illustrated in FIG. 4 by the arrow.

The articultor 10 is removably mounted on the mounting plate 12 by means of a 3-point mounting system comprising locator pins 44 and 46 (See FIGS. 1, 4-6, and 8-10) and a threaded locking screw 48. The 3-point arrangement provides for simple and fast mounting and dismounting of the articulator on the plate 12. Obviously, other mounting systems can be used in conjunction with plate 12 which itself is merely illustrative of a base surface for the articulator 10.

Referring now to FIGS. 5 and 6, the mandibular model 34 is shown in the malocclusion position in FIG. 5 and in the proposed corrective or "normal" occlusion position in FIG. 6. The structural components illustrated in FIGS. 5 and 6 are identical except for the intermediate locking templates 36b and 36c which have the receptacle 42 positioned at different locations with respect to the articulator base 14.

The templates 36b and 36c are produced by conventional dental casting techniques. The mandibular model 34 is positioned as shown in FIG. 5 with respect to the upper jaw model 32 using a bite registration obtained from the patient and temporarily held in that position by suitable means (not shown). A form (not shown) is fitted around the articulator base 14 accommodating the base 36a of the mandibular model. The mold space in the form is then filled with a suitable casting material which when cured produces the template 36b. It will be appreciated that by using this technique, the template 36b accurately records the three dimensional coordinates of the mandibular model 34 in the malocclusion position.

The same technique is employed to produce the corrective template 36c. However, the mandibular model 34 is positioned in the desired corrective position with respect to the upper jaw model 32, as shown in FIG. 6 before the casting material is then placed in the mold space in the form. The pair of templates together record the translational and rotational movements embodied in the corrective procedure.

Given the positional relationships of the articulator base 14, locking template 36 and the mandibular model 34, it is possible to produce two unique positions for the mandibular model that represent the corrective i.e. "normal" and the malocclusion positions. The two positions are achieved by using the appropriate intermediate locking template 36b or 36c between the articular base 14 and the mandibular model 34.

Referring now to FIGS. 7-10 there is shown a dental surveyor constructed in accordance with the present invention and indicated generally by the reference numeral 50. The surveyor has a flat, circular base plate 52 that is mounted on the maxillary model by means of a pair of locking pins 54 and an adjustable locking screw 56. A radius arm 58 is pivotally mounted with respect to the base plate 52 by means of a pivot screw 60. The rotational position of the radius arm with respect to the circumference of the base plate 52 can be adjusted by loosening wing nut 62 and rotating the arm 58 to the desired position. When the desired position is reached, the arm is locked with respect to the base plate 52 by tightening wing nut 62.

Figure 7:
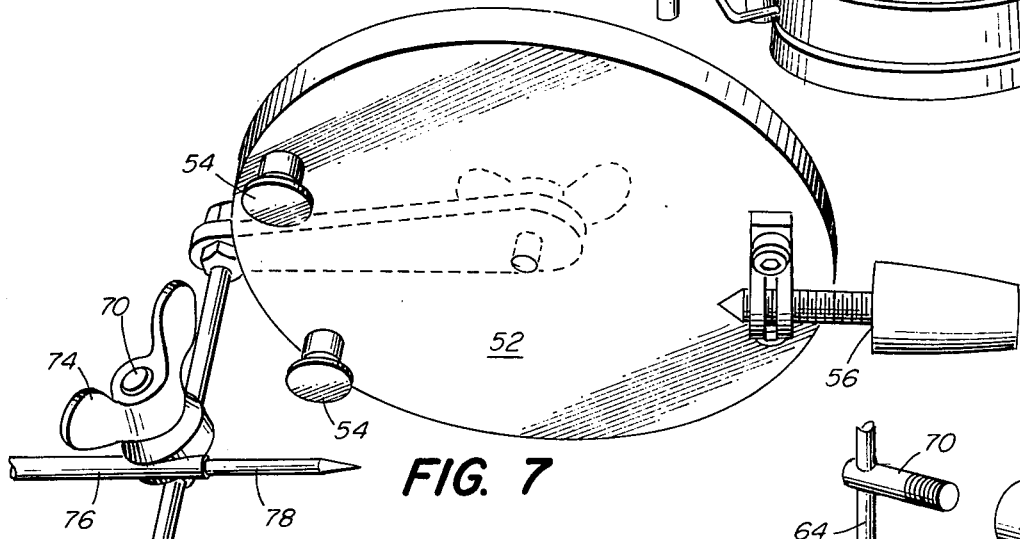
FIG. 7 is a view in perspective of the dental surveyor of the present invention.
Figure 8:
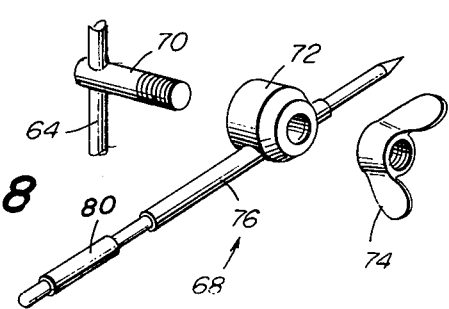
FIG. 8 is an exploded view in perspective of the stylus assembly of the dental surveyor depicted in FIG. 7.

A threaded stylus assembly support rod 64 is secured with respect to the radius arm 58 by means of an acorn nut 66. It can be seen in FIGS. 7, 9 and 10 that the radius arm 58 is parallel to the plane of base plate 52 and that the axis of the stylus assembly support rod 64 is normal to the plane of the base plate 54. The stylus assembly, indicated generally by the reference numeral 68, in FIG. 8, is best shown in FIGS. 7 and 8. The assembly 68 comprises a toggle bolt 70 that is slidably and rotatably mounted on the assembly support rod 64. An apertured locking collar 72 is fitted over the toggle bolt 70 and removably locked against the rod 64 by means of wing nut 74. The locking collar 72 includes a sleeve 76 through which is slidably mounted, a stylus or scribe 78. Preferably, the outer end of slide 78 has an operator finger grip 80.

Figure 9:
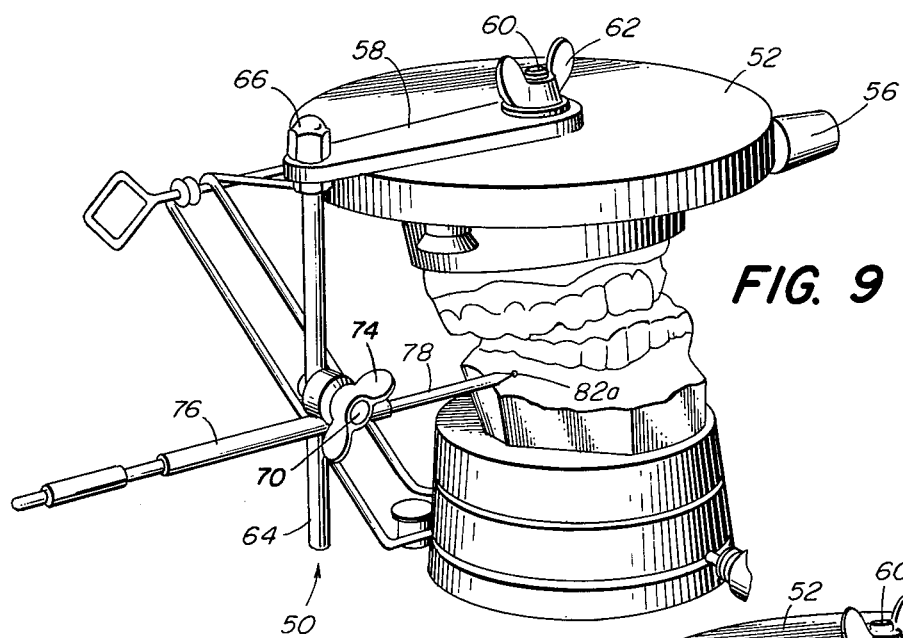
FIG. 9 is a view in perspective showing the dental surveyor of FIG. 6 mounted on an articulated maxillary model with the corresponding mandibular model located in the malocclusion position; and, FIG. 10 is a view similar to that of FIG. 9, but illustrating the mandibular model in the proposed corrective occlusion position.

Looking now at FIG. 9, it will be appreciated that the vertical position of the stylus assembly 68 can be adjusted by loosening wing nut 74 and then sliding the assembly either upwardly or downwardly on support rod 64. In addition to the vertical adjustment the stylus assembly 68 can be rotated about the vertical axis of support rod 64 and pivoted about the horizontal axis of the toggle bolt 70. Given these movements, together with the rotational adjustment of the radius arm 58, it is possible to position the slidably movable scribe or stylus 78 at any position on either the mandibular or maxillary models.

Figure 10:
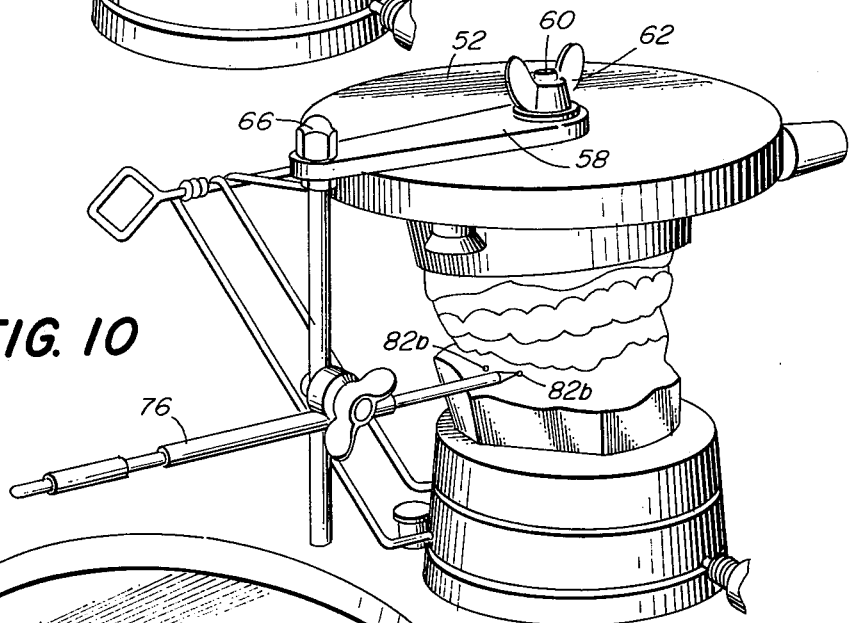

Assuming for purposes of illustration, that the mandibular model is positioned within the template that corresponds to the malocclusion position, as shown in FIG. 9, the scribe 78 can be moved to the right until it contacts a selected point 82a on the mandibular model. This point can be scratched or otherwise marked to provide a permanent visual record. If the scribe is now withdrawn from the model and the mandibular model and locking template removed from the articulator, the mandibular model can then be remounted on the articulator using the template that corresponds to the proposed corrective occlusion as shown in FIG. 10. The scribe is then moved to the right to engage the mandibular model in the new position thereby creating a new point 82b, as shown in FIG. 10. This point can be scratched or otherwise marked to provide a permanent visual record.

It will be appreciated that by drawing a line between points 82a and 82b, the surgeon can obtain a visual indication of both the direction and magnitude of movement of point 82a in order to position that anatomical point of interest at point 82b after the corrective surgery. With the visual indication of the movement of the point on the mandibular model as shown in FIG. 10, one can determine the translational movements that are required to move the anatomical point of interest 82a from the position shown in FIG. 9 to that shown in FIG. 10.

Although the movement of only one point has been illustrated in the drawings, it will be understood by those skilled in the art that the dental surveyor can be used to plot the movements of a number of points on the mandibular model, from which rotational movement can be determined. In a like manner, movement of the maxilla with respect to the mandible can be determined simply by inverting the articulated models in the surveyor. In this case, the locking templates would have been fabricated for the maxillary model.

Having described in detail a preferred embodiment of my invention, it will now be apparent to those skilled in the art that numerous modifications can be made therein without departing from the scope of the invention as defined in the appended claims.

What I claim and desire to secure by Letters Patent of the United States is:

1. A method for preoperative evaluation comprising the steps of:
   1. preparing maxillary and mandibular dental models, said models each having a base portion of a given configuration;
   2. mounting a articulator base on a dental articulator, said articulator base having at least one positional keying means;
   3. placing said models on the articulator in a first position that presents the patient's malocclusion and then temporarily securing the models in said first position;
   4. casting a first template means having (i) a complementary replica of the base portion of one of said dental models when the model is in such first position and (ii) at least one positional keying means that mates with said at least one positional keying means of said articulator base;
   5. detaching said dental models from said first position;
   6. placing said dental models on the articulator in a second position that presents the patient's proposed corrective position and then temporarily securing the models in said second position;
   7. casting a second template means having (i) a complementary replica of the base portion of said one of said dental models when the model is in said second position and (ii) at least one positional keying means that mates with said at least one positional keying means on said articulator base;
   8. unsecuring said dental models from said second position;
   9. placing the base of one of said dental models in the complementary replica thereof in one of said template means and engaging the positional keying means thereof with the positional keying means of articulator base;
   10. mounting a stylus assembly with respect to one of said dental models, said stylus assembly including a movable stylus;
   11. marking at least one of said dental models with the stylus;
   12. substituting the other of said template means for said one of said template means without moving the stylus assembly relative to said one of said dental models;
   13. marking again said at least one of said dental models with the stylus; and,
   14. determining from the two stylus marks the translational movements required to move said one of said models from the first position to the second position.

2. The method of claim 1 further comprising the step of drawing a line between said two stylus marks and measuring the length of the line.

3. The method of claim 1 further comprising the step of marking both of said dental models with the stylus when said one of said models is in the first position and again when it is in the second position.

4. The method of claim 1, further comprising the steps of marking said at least one of said dental models with another stylus mark when the dental model is in each of said first and second positions and determining from the resulting two pairs of stylus marks, the rotational movement of the dental model from the first position to the second position.

* * * * *